United States Patent [19]

Lefebvre

[11] Patent Number: 5,649,953
[45] Date of Patent: Jul. 22, 1997

[54] KIT FOR MEDICAL USE COMPOSED OF A FILTER AND A DEVICE FOR PLACING IT IN THE VESSEL

[75] Inventor: Jean-Marie Lefebvre, Lille, France

[73] Assignee: Bentex Trading S.A., Luxembourg

[21] Appl. No.: 406,913

[22] PCT Filed: Sep. 14, 1993

[86] PCT No.: PCT/FR93/00884

§ 371 Date: May 9, 1995

§ 102(e) Date: May 9, 1995

[87] PCT Pub. No.: WO94/07431

PCT Pub. Date: Apr. 14, 1994

[30] Foreign Application Priority Data

Sep. 28, 1992 [FR] France ............... 92 11915

[51] Int. Cl.⁶ ................................................. A61M 29/00
[52] U.S. Cl. ........................ 606/200; 606/191; 604/104; 604/106
[58] Field of Search ............... 606/200; 604/104, 604/159, 167, 264, 130, 21, 26, 51, 52, 18, 36, 5, 6, 187

[56] References Cited

U.S. PATENT DOCUMENTS

| | | |
|---|---|---|
| 3,952,747 | 4/1976 | Kimmell, Jr. . |
| 4,425,908 | 1/1984 | Simon ................................. 606/200 |
| 4,943,297 | 7/1990 | Saveliev et al. ..................... 606/200 |
| 4,969,891 | 11/1990 | Gewertz ............................. 606/200 |
| 4,990,156 | 2/1991 | Lefebvre ............................ 606/200 |
| 5,011,488 | 4/1991 | Ginsburg ............................ 604/104 |
| 5,108,418 | 4/1992 | Lefebvre ............................ 606/200 |
| 5,133,733 | 7/1992 | Rasmussen et al. ................ 606/200 |
| 5,147,379 | 9/1992 | Sabbaghian et al. ............... 606/200 |
| 5,151,105 | 9/1992 | Kwan-Gett ......................... 604/96 |
| 5,152,777 | 10/1992 | Goldberg et al. ................... 606/200 |

FOREIGN PATENT DOCUMENTS

| | | |
|---|---|---|
| 0408245 | 1/1991 | European Pat. Off. . |
| 2567405 | 1/1986 | France . |
| 2580504 | 10/1986 | France . |

*Primary Examiner*—John G. Weiss
*Assistant Examiner*—Ki Yong O
*Attorney, Agent, or Firm*—Ladas & Parry

[57] ABSTRACT

A medical kit comprises: a) a filter consisting of elastic lugs deployed substantially in the form of a conical corolla emerging rearwardly from a distal head, and having a small orifice of diameter D1 at its end; b) a metal guide of outside diameter D2; c) a push rod consisting of a hollow tube having an internal opening of diameter D3; d) an insertion tube fitted at its distal end with a rigid cylindrical cap of inside diameter D4, and having an internal annular shoulder towards its proximate end capable of serving as a stop for the ends of the filter tabs. The respective dimensions of the various elements are such that D4>D3>D1>D2.

6 Claims, 1 Drawing Sheet

KIT FOR MEDICAL USE COMPOSED OF A FILTER AND A DEVICE FOR PLACING IT IN THE VESSEL

FIELD OF THE INVENTION

The present invention relates to the filtration of clots circulating in the bloodstream. It relates more particularly to an assembly consisting of a filter and a device for inserting it in the vessel.

To prevent the migration of clots originating from the lower veins of the body into the heart and pulmonary artery, and hence to avoid an embolism, it is known to implant filter devices, hereafter called filters, the purpose of which is to obstruct the passage of clots while at the same time allowing the blood to flow through the vessel.

BACKGROUND OF THE INVENTION

There are numerous types of filter in existence. The so-called GREENFIELD filter, which consists of wires preformed into zig-zags and joined together by a cover, is particularly well known. These wires are arranged to form a cone whose tip is the cover, said zig-zags forming the envelope of the cone. The ends of the wires are provided with anchoring hooks by which the filter can grip the inner wall of the vessel.

The placing of such a filter is effected from an insertion sheath inside which the filter is inserted, the elastic wires being kept approximately in alignment with the longitudinal axis of the sheath. After the distal end of the insertion sheath has been positioned at the location where the filter is to be placed in the vessel, said filter is released with the aid of a thrust component which is a rod capable of being actuated from outside the insertion sheath, and which, bearing on the filter, makes it possible to move the latter while at the same time keeping the insertion sheath steady. Once released in the vessel, the elastic wires develop into a cone inside the vessel, the end hooks on the wires gripping the inner wall of the vessel.

Other filters based on the same working principle have been proposed since this GREENFIELD filter, one having a conical general shape with several lugs joined together at their heads, forming an ogival point and diverging towards their other end. This filter is in a single piece formed from a thin sheet of a material of appropriate elasticity. The lugs in question are therefore flat strips of small thickness. Such lugs are tapered at their free end. For positioning inside the vessel, this filter is placed in an insertion tube. A flexible metal guide is first introduced into the vein; then, using this metal guide, a first, relatively thin insertion tube is introduced which is used as a guide tube for the passage of the insertion tube containing the filter.

Thus, as well as the flexible metal guide, the placing of such a filter requires the use of two insertion tubes.

The Applicant has found various disadvantages to be associated with the devices currently in use. On the one hand, the first insertion tube, through which the second insertion tube containing the filter has to travel, must have a relatively large overall diameter because the second insertion tube can have an internal diameter of 3.6 mm. Thus the first insertion tube may possibly have an external diameter of the order of 5 mm. These tubes are made of a flexible plastic material which must nevertheless be sufficiently rigid to be able to advance inside the vessel while at the same time delimiting an interior space capable of accommodating the second insertion tube. Depending on the sinuosity of the vessels, especially in the case of the left femoral vein, the first insertion tube sometimes becomes prohibitively bent, preventing the second insertion tube from traveling through it normally.

The object which the Applicant set out to achieve is to propose a kit, composed of a filter and a device for placing it, which overcomes the observed disadvantages in that it is of simple design and does not require insertion tubes of large diameter.

This object is perfectly achieved by the kit of the invention, which is composed of a filter, a flexible metal guide, a push-rod and an insertion tube. The filter is formed by elastic lugs extending approximately in the shape of a conical corolla extending from a distal head, which has a small orifice of diameter D1 in its tip; the metal guide has an external diameter D2; the push-rod is a hollow tube of internal diameter D3; the insertion tube, which is made of plastic, is fitted at its distal end with a rigid cylindrical cap of internal diameter D4. The cap has an annular internal set-back at its proximal end, which is capable of acting as a stop for the ends of the lugs of the filter. This annular set-back also serves to center the push-rod. The respective dimensions of the different components mentioned above are such that D4 is greater than D3>D1>D2, so that, in the position of insertion of the filter into the vessel, the tip of the filter is facing forwards, the ends of its lugs being folded back inside the cap, and the distal end of the push-rod bearing against the inner part of said tip.

The placing of the filter by means of the kit of the invention is effected by first introducing the flexible metal guide into the vessel and then threading the filter itself, which is positioned at the end of the insertion tube, over said guide, the lugs being folded back and placed inside the cap which terminates said insertion tube. Thus it is seen that when the assembly consisting of the filter, the insertion tube and the push-rod travels into the vessel, the filter itself is not enclosed in an insertion tube but is outside it. Only the free ends of the lugs of the filter are locked in the cap between the inner face of said cap and the outer surface of the push-rod.

It is seen that, under these conditions, the insertion tube can have a smaller diameter, for example of the order of 3 mm.

By keeping the flexible metal guide inside the vessel during the introduction of the other components of the kit, it is possible to avoid any risk that the filter will become stuck in the sinuosity of the vessel. It may also be pointed out that the filter, held solely by the free end of its lugs, has a degree of flexibility which facilitates the passage of this assembly through the particularly sinuous parts of the vessel. It is of course important for said lugs to be adequately held between the cap and the push-rod. For this purpose, the cap has a length of at least 10 mm for a lug length of between 40 and 60 mm.

The filter preferably has six lugs whose width at the proximal end is approximately equal to or less than half the internal diameter D4 of the cap. Thus, in the folded-back position, the six lugs are contiguous and form a regular hexagon approximately inscribed in the cap.

In the case where the ends of the lugs have means of anchoring to the inner wall of the vessel, these means preferably consist of two hooks pointing in opposite directions. More precisely, each hook is obtained by the cutting-out of a triangular portion of the strip forming the distal end of the lug; moreover, it has an elbow-shaped configuration relative to the plane of said lug. This particular arrangement reduces the height of said hook outwardly of the lug and consequently reduces the space which is required between the push-rod and the cap for accommodating each lug when the filter is positioned. However, this configuration in no way reduces the good grip of the filter on the wall of the vessel.

To avoid any false maneuvers in the placing of the filter, the insertion tube is terminated at its distal end by a shoulder which is intended to remain outside the patient's body; furthermore, the kit has a hollow protective cover which can be firmly fixed to said shoulder, for example by screwing, and which covers the proximal end of the push-rod, the latter extending beyond the insertion tube when said cover is in the fixed position. Thus the operator cannot move the push-rod accidentally; to move it, he has to release the protective cover and remove it in order to have access to the proximal end of the push-rod.

BRIEF DESCRIPTION OF THE DRAWINGS

The invention will be understood more clearly from the following description of an embodiment of the filtration kit for medical use, composed of a flexible metal guide, a filter, a push-rod and an insertion tube, illustrated by the attached drawing in which.

DETAILED DESCRIPTION OF THE DRAWINGS

Figure 1:
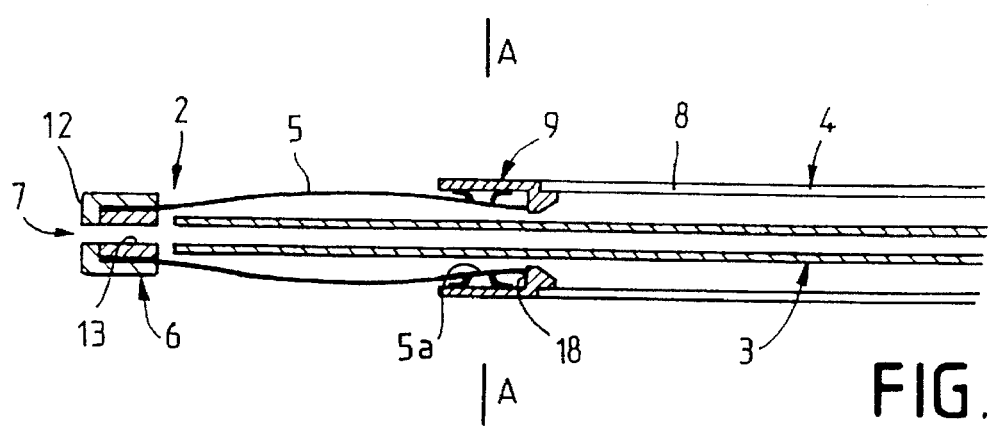
FIG. 1 is a diagrammatic section of the filter prepositioned in the cap terminating the distal end of the insertion tube.

The filtration kit for medical use according to the invention is composed of four components, namely a flexible metal guide 1, a filter 2, a push-rod 3 and an insertion tube 4.

The metal guide is well known in other connections, being already in common use. It is a flexible wire of given external diameter D2.

The filter 2 is formed of elastic lugs 5 fixed to the distal head 6 of the filter. This head 6 has a passage orifice 7 of internal diameter D1, which is greater than the abovementioned diameter D2.

The push-rod 3 is a hollow flexible tube whose internal diameter is slightly greater than D2. The external diameter of the push-rod is referred to as D3.

The insertion tube 4 is a flexible plastic sheath 8 terminated by a rigid cap 9. The latter is for example a small cylindrical metal tube to which the end of the sheath 8 is fitted under the action of heat. The cap 9 has an internal diameter D4 which is substantially greater than the external diameter D3 of the push-rod 3. It has an annular set-back 18 at its proximal end, i.e. at the end attached to the insertion tube 4.

FIG. 1 shows the filter 2 prepositioned on the insertion tube 8. In this configuration, the head 6 of the filter is facing forwards, i.e. towards what will be the distal end after introduction into the vein. The lugs 5 are pulled back longitudinally along the axis of the filter and are introduced inside the cap 9. They essentially butt against the annular internal set-back 18 at the bottom of the cap 9. The push-rod 3 is placed inside the insertion tube 4, passes through the hollow space inside the annular set-back 18, which helps to center it in the cap 9, and extends beyond the distal end of said insertion tube until it comes into contact with the internal part of the head 6.

Figure 4:
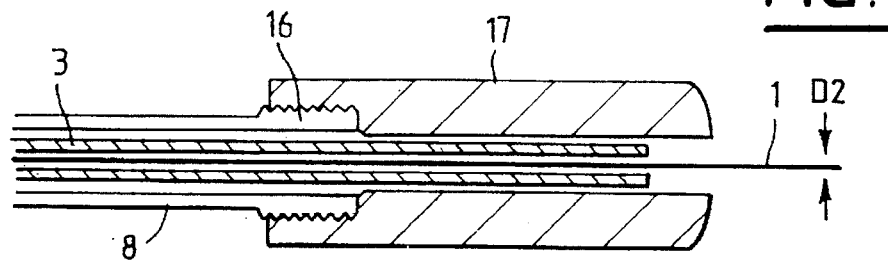
FIG. 4 is a diagrammatic section of the proximal end of the kit.

FIG. 4 shows the proximal end of the kit, which is intended to remain outside the patient's body. The insertion tube 4 is terminated by a threaded shoulder 16 to which a protective cover 17 is firmly fixed by screwing. This cover 17 is hollow and extends beyond the distal end of the push-rod 3.

To place the filter inside the vein, the metal guide 1 is first introduced as far as the location where the filter 2 is to be positioned.

Once this has been done, the filter 2, the push-rod 3 and the insertion tube 4, as shown in FIGS. 1 and 4, are threaded over the proximal end of the guide, which is therefore located outside the patient's body. This threading operation is carried out by pushing said proximal end of the guide 1 successively through the orifice 7 in the head 6 of the filter 2 and through the hollow space inside the push-rod 3.

This assembly made up of the filter 2, the push-rod 3 and the insertion tube 4 is pushed into the vein as far as the location where the filter 2 is to be positioned.

The filter 2 is released by holding the insertion tube 4 steady and moving the push-rod 3 forwards. This can only be done after the protective cover 17 has been unscrewed, thereby giving the operator access to the proximal end of the push-rod 3. This movement pushes the head 6 of the filter 2, and with it the end 5a of the lugs 5 inside the cap 9, until said ends 5a come out of said cap.

The lugs 5, now freed from their entrapment in the cap 9, develop the shape of a corolla by virtue of their natural elasticity, and the filter 2 forms a cone, the ends 5a of the lugs 5 bearing on the inner wall of the vein.

In a preferred embodiment, the filter 2 is formed of six elastic lugs 5. These are metal strips which have been preformed and heat-treated so that, in the normal position, they have an outwardly bent shape shown in FIG. 2. The head 6 of the filter is made up of two parts 12, 13: an outer hollow part 12 and a second inner cylindrical part 13. The lugs 5, arranged symmetrically and attached to one another over the inner periphery of the first part 12, are locked in position by the introduction of the second cylindrical part 13.

Figure 2:
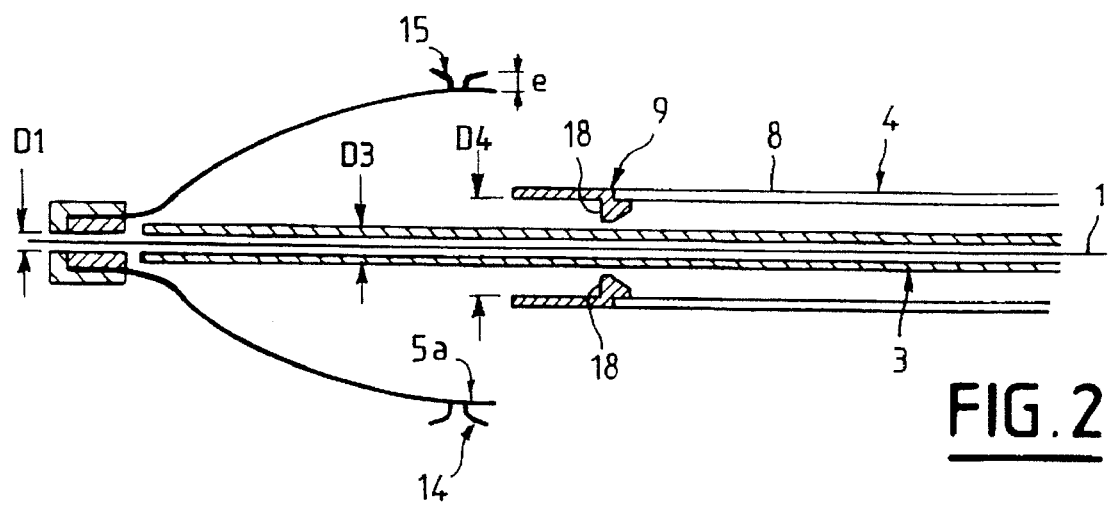
FIG. 2 is a diagrammatic section of the filtration kit after the filter has been released inside the vein.

The filter 2 also possesses anchoring hooks 14, 15 situated at the free ends 5a of the lugs 5. Each lug 5 preferably has two hooks, 14 and 15, inclined in opposite directions, as illustrated in FIG. 2.

Advantageously, each hook is obtained by the cutting-out and bending of a V-shape made in the central zone of the relatively proximal end 5a of each lug 5.

Figure 3:
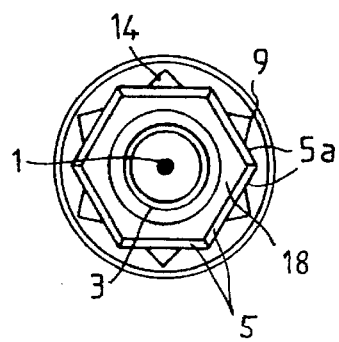
FIG. 3 is a cross-section of the cap, the filter, the push-rod and the guide along the line A,A of FIG. 1.

FIG. 3 shows a filter comprising six lugs 5 whose width is substantially less than half the internal diameter D4 of the cap 9. Thus, once positioned inside the cap 9, the ends 5a of these six lugs 5 take up a position in the shape of a regular hexagon.

Advantageously, the hooks 14 have an elbow 15, reducing their height e relative to the plane of the lug 5a. This height e preferably corresponds approximately to the height of the arc of the regular hexagon inscribed in the circle, representing the inner face of the cap 9.

Choosing these characteristics makes it possible to optimize the accommodation of the end 5a of the lugs 5 inside the cap 9 and around the push-rod 3 so as to obtain a homogeneous release of the filter 2 inside the vein under the action of the push-rod 3.

The invention is not limited to the embodiment which has now been described by way of a non-exhaustive example. In particular, it would be possible to use other types of filter than that described in detail, provided that the diameter of the orifice in the tip is greater than that of the metal guide, so as to allow the latter to pass through, but smaller than the external diameter of the push-rod, so that the latter can bear on the inner face of said tip.

What is claimed is:

1. A kit for medical use, comprising a filter adapted to be inserted into a vein, a flexible metal guide, a push-rod and an insertion tube, in which a) the filter, which includes radially expandable elastic lugs each having a distal end and a proximal end, said distal ends of said lugs extending outwardly approximately in a shape of a conical corolla, said distal ends of said lugs are capable of being folded inwardly, said proximal ends of said lugs are joined at a head which has a small circular orifice of diameter D1 to receive said guide,
   b) the metal guide formed from a flexible wire has a cross-sectional diameter D2,
   c) the push-rod having a distal end is a hollow tube of internal diameter D3, and receives said guide therein,
   d) the insertion tube having a distal end is hollow and surrounds said push-rod, wherein said distal end of said lugs are capable of being folded inwardly and received in said distal end of said insertion tube; said distal end of said insertion tube having a rigid cylindrical cap of internal diameter D4, said cap having an annular internal shoulder at a distal end, which is capable of acting as a stop for said distal end of the lugs of the filter, diameters of each component being such that D4>D3>D1>D2, such that when said distal ends of said lugs are folded back inside said cap, the distal end of said push rod bears against said head.

2. A kit for medical use according to claim 1, wherein the cap has a length of at least 10 mm for a lug length of between 40 and 60 mm.

3. A kit for medical use according to claim 1, wherein the filter has six lugs whose width at its proximal end is approximately equal to or less than half the internal diameter D4 of the cap.

4. A kit for medical use according to claim 1, wherein each end of the lugs has two outwardly bent hooks pointing in opposite directions.

5. A kit for medical use according to claim 4, wherein each hook has an elbow-shaped configuration in cross section.

6. A kit for medical use according to claim 1, wherein the insertion tube is terminated at a proximal end by a shoulder threaded into a hollow protective cover.

\* \* \* \* \*